(12) United States Patent
Hwang et al.

(10) Patent No.: US 7,953,474 B2
(45) Date of Patent: May 31, 2011

(54) APPARATUS, METHOD AND OPTICAL SENSOR MODULE USING A TILTER FOR BODY FAT MEASUREMENT

(75) Inventors: In Duk Hwang, Yongin-si (KR); Sang Ryong Kim, Yongin-si (KR); Kun Soo Shin, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 499 days.

(21) Appl. No.: 11/808,755

(22) Filed: Jun. 12, 2007

(65) Prior Publication Data

US 2008/0021330 A1 Jan. 24, 2008

(30) Foreign Application Priority Data

Jul. 21, 2006 (KR) .................. 10-2006-0068482

(51) Int. Cl.
*A61B 6/00* (2006.01)
*A61B 5/00* (2006.01)
(52) U.S. Cl. ...................................... 600/476; 600/310
(58) Field of Classification Search .................. 600/317, 600/323, 476
See application file for complete search history.

(56) References Cited

U.S. PATENT DOCUMENTS

| | | | |
|---|---|---|---|
| 4,223,680 A | 9/1980 | Jöbsis | |
| 6,050,688 A * | 4/2000 | Grinblat | 351/214 |
| 6,556,851 B1 * | 4/2003 | Ott et al. | 600/310 |
| 2003/0220549 A1 | 11/2003 | Liu et al. | |
| 2005/0002031 A1 * | 1/2005 | Kraemer et al. | 356/337 |
| 2005/0075549 A1 * | 4/2005 | Kondoh et al. | 600/323 |

FOREIGN PATENT DOCUMENTS

| | | |
|---|---|---|
| EP | 1366707 A1 | 12/2003 |
| EP | 1520514 A1 | 4/2005 |
| JP | 2003-310575 | 11/2003 |
| JP | 2004-350836 | 11/2004 |
| WO | WO 00/33730 | 6/2000 |
| WO | 2005/002437 | 1/2005 |

OTHER PUBLICATIONS

European Search Report for corresponding European Patent Application No. 07112765.8 dated Oct. 2, 2007, 6 pages (in English).

* cited by examiner

*Primary Examiner* — Long V Le
*Assistant Examiner* — Michael T Rozanski
(74) *Attorney, Agent, or Firm* — Staas & Halsey LLP

(57) ABSTRACT

An apparatus, method and optical sensor module for body fat measurement includes at least one light source, a tilter to control an irradiation angle of the light source to radiate light from the light source into biological tissue at a predetermined angle, and an optical detector to detect an optical signal scattered from the biological tissue, and transform the scattered optical signal into an electric signal to acquire more accurate body fat information about a deep body fat layer.

18 Claims, 4 Drawing Sheets

APPARATUS, METHOD AND OPTICAL SENSOR MODULE USING A TILTER FOR BODY FAT MEASUREMENT

CROSS-REFERENCE TO RELATED APPLICATIONS

This application claims the benefit of Korean Patent Application No. 10-2006-0068482, filed on Jul. 21, 2006, in the Korean Intellectual Property Office, the disclosure of which is incorporated herein by reference.

BACKGROUND

1. Field

An embodiment of the present invention relates to an apparatus, method and optical sensor module for body fat measurement. More particularly, an embodiment of the present invention relates to an apparatus and an optical sensor module having a tilter, and a method for using the apparatus and/or sensor for body fat measurement. The tilter may be made of a material having a similar refraction index to a biological tissue of a body fat measurement object, and enables light radiated from a light source to irradiate the biological tissue at a predetermined incident angle, allowing deeper penetration of the light into the tissue.

2. Description of the Related Art

Maintaining health and achieving beauty is a priority for many consumers. Accordingly, there is currently a trend to seek a healthy lifestyle. The amount of body fat is one criteria used to estimate an individual's health. With this in mind, there are various methods of measuring the amount of body fat, with the body fat ratio being a common criteria used to measure the amount of body fat and to estimate an individual's health or as a measure of beauty such as with dieting.

Methods for measuring body fat ratio include a body average density measurement employing underwater weighing, a skinfold test measuring the thickness of fat at a specific point of the body, applying a weak electrical current to the body and measuring the body's impedance, and using a table of values to measure the body fat ratio based on waist size, height, body type, etc. Problems associated with these methods include inaccuracy and the need for complicated equipment.

Recently, certain body fat measurement methods have used a light capable of readily and accurately measuring body fat. A body fat measurement device using light is based on a theory that when light is emitted from a light source to irradiate a measurement point of a body, backward scattering occurs in the body, and subsequently body fat is measured by measuring a scattered optical signal using an optical detector.

An important consideration is whether the optical signal penetrates and scatters deep within the biological tissue, i.e. up to a muscle layer at the measurement point. Generally, when the depth of the incident light increases, the distance between the light source and the optical detector also increases making it difficult to employ a portable body fat measurement apparatus. Thus, it is difficult to accurately measure body fat using such conventional portable body fat measurement apparatuses.

Accordingly, the inventors have found a need for a portable body fat measurement apparatus that can readily and accurately measure the body fat of a body.

SUMMARY

An aspect of one or more embodiments of the present invention provides an optical sensor module for a body fat measurement apparatus, the module may include, for example, at least one light source, a tilter to control an irradiation angle of the at least one light source to radiate light from the at least one light source into biological tissue at a predetermined angle, and an optical detector to detect a scattered optical signal, the signal scattered from the light radiated into the biological tissue.

Another aspect of one or more embodiments of the present invention provides a body fat measurement apparatus including, for example, at least one light source, a tilter to control an irradiation angle of the at least one light source to radiate light from the at least one light source into a biological tissue at a predetermined angle, an optical detector to detect a scattered optical signal, the signal scattered from the light radiated into the biological tissue, and to transform the scattered optical signal into an electric signal, and an electric signal calculation unit to process the electric signal and to calculate body fat information.

Another aspect of one or more embodiments of the present invention provides a method for measuring body fat, the method including, for example, irradiating light into a biological tissue at a predetermined angle other than an angle perpendicular to the biological tissue, detecting scattered light from the irradiating of the light into the biological tissue, and transforming the detected scattered light into an electrical signal.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EMBODIMENTS

Figure 1:
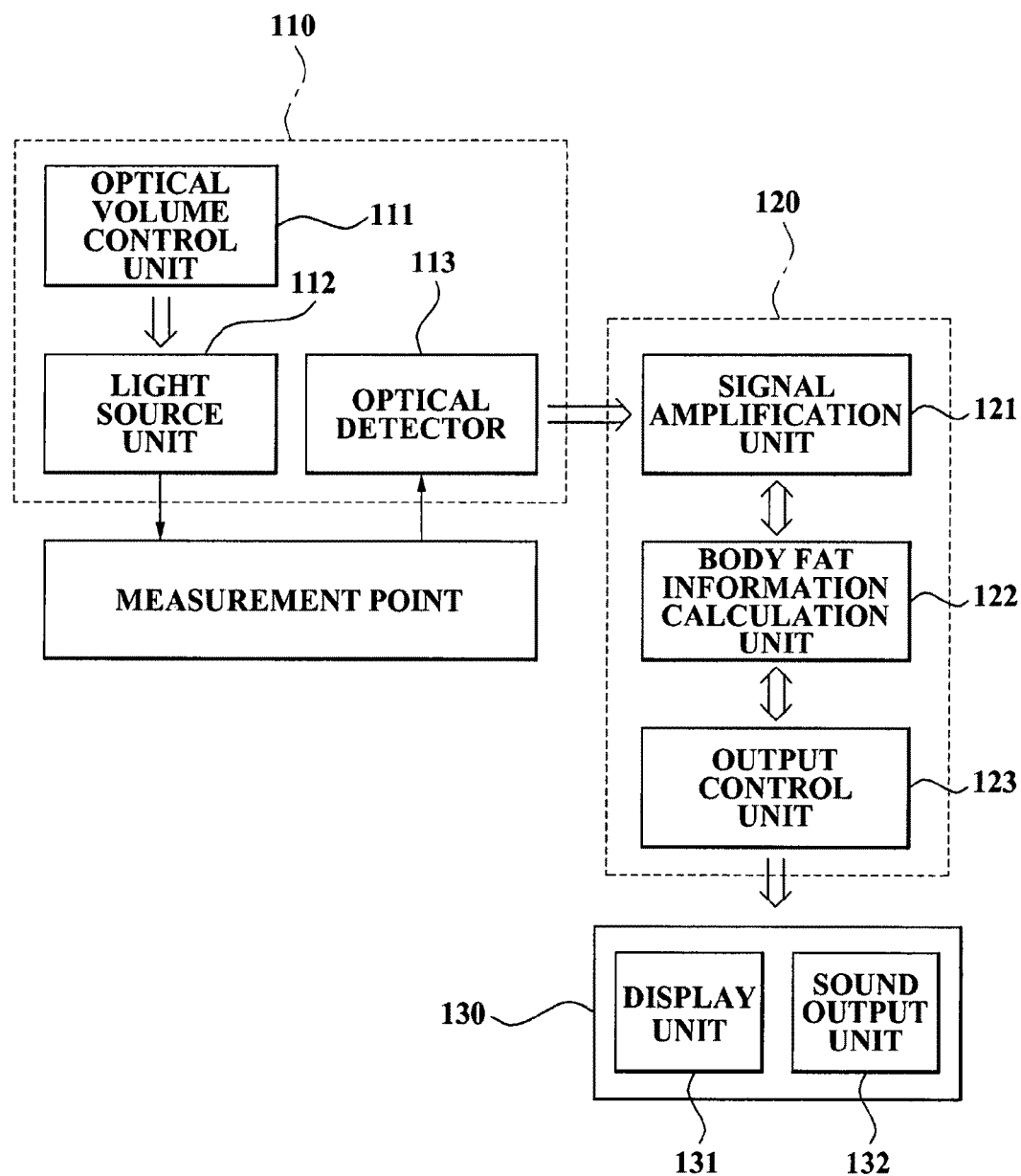
FIG. 1 illustrates a body fat measurement apparatus having an optical sensor module, according to one or more embodiments of the present invention.

Reference will now be made in detail to embodiments of the present invention, examples of which are illustrated in the accompanying drawings, wherein like reference numerals refer to like elements throughout. Embodiments are described below in order to explain the present invention by referring to the figures.

An apparatus, method and optical sensor module of a body fat measurement apparatus in accordance with one or more embodiments of the present invention is illustrated in FIGS. 1-4. The apparatus may include an optical sensor module 110, a signal processing unit 120, and an output unit 130, for example. The optical sensor module 110 my further include an optical power control unit 111, at least one light source unit 112, a tilter 211, and an optical detector 113, for example, noting that such modules may equally include differing numbers and types of components in other configurations. According to an embodiment, the corresponding method measures body fat using at least one light source and a tilter to control an irradiation angle of the at least one light source so that light is radiated into a biological tissue at a predetermined angle. The one or more embodiments of the present invention described herein provide a number of advantages including enhanced accuracy and the ability to acquire body fat information about a deep body fat layer.

In an embodiment, a portable body fat measurement device may be embodied within, or as any one of, a mobile terminal, a personal digital Assistant (PDA), a portable game device, an MP3 player, a personal multimedia player (PMP), a digital multimedia broadcasting terminal (DMB) terminal, a portable blood sugar measurement device or a grip power exercise device, for example. Conversely, the portable body fat measurement device/apparatus may not be installed in such devices, but may be designed in a stand-alone configuration, or implemented as a system.

Also, the biological tissue described herein is not be limited to a human body, i.e., the portable body fat measurement device, according to differing embodiments, may be used for all organisms having a subcutaneous fat layer between skin and muscle.

Referring to FIG. 1 again, the electrical signal process unit 120 may include a signal amplification unit 121, a body fat information calculation unit 122 and an output control unit 123, for example. Additionally, the output unit 130 may include a display unit 131 and a sound output unit 132.

Again, the light source unit 112 of the optical sensor module 110 may include at least one light source and a tilter, which may be provided together with the light source. The light source may be embodied as any one of a point light source, including a top view light emitting diode (LED) which has been popularly utilized, or a surface light source, for example. A configuration of the light source unit 112 will be described in greater detail by referring to FIG. 2.

Figure 2A:
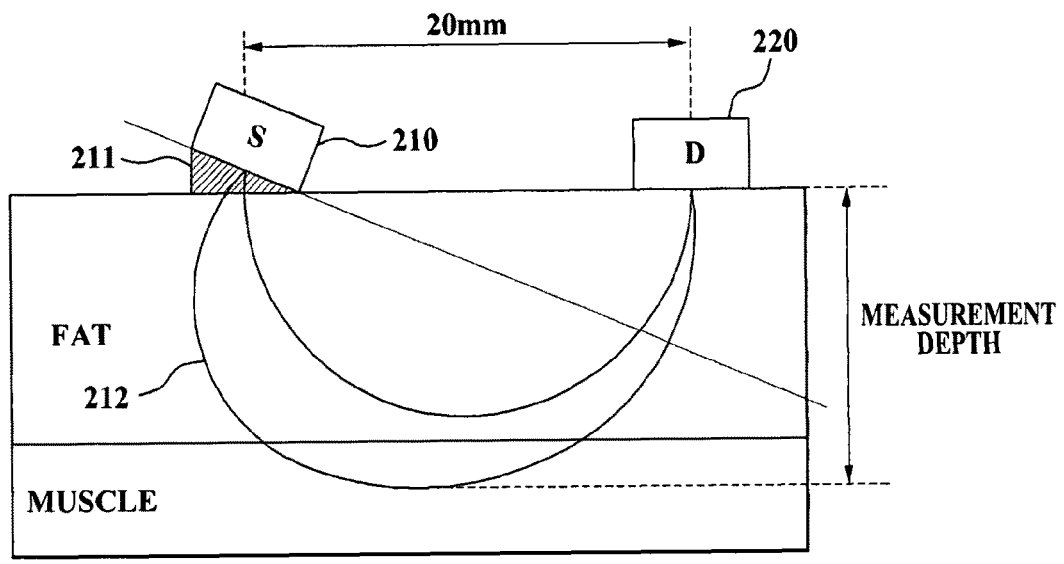
FIG. 2A illustrates an optical sensor module, such as that of FIG. 1, having a light source unit with a tilter, according to one or more embodiments of the present invention.
Figure 2B:
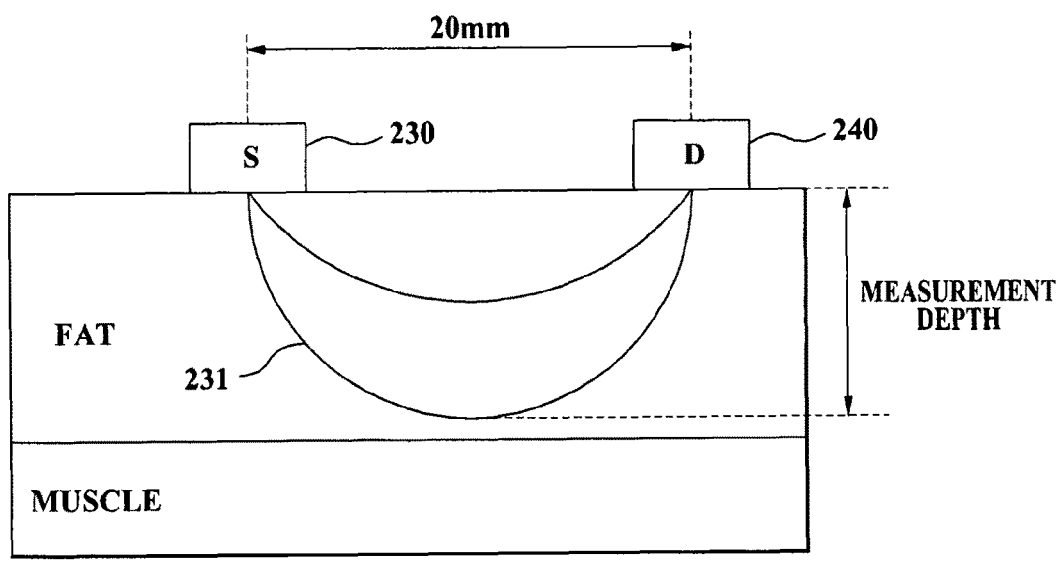
FIG. 2B illustrates a light sensor module having a light source unit without a tilter, according to one or more embodiments of the present invention.

FIG. 2A illustrates an optical sensor module, such as that of FIG. 1, having a light source unit with a tilter 211, and FIG. 2B illustrates an optical sensor module having a light source unit without such a tilter 211.

Referring to FIG. 2A, the tilter 211 may be combined with the light source 210 of the optical sensor module. Specifically, the tilter 211 may be positioned at a surface where the light source 210 contacts a biological tissue. Thus, the tilter 211 may be placed between the surface of the light source 210 and the biological tissue so that light incident upon the tissue from the light source falls at an angle other than one perpendicular to the tissue.

As an example, as illustrated in FIG. 2A, when the light source 210 is a type of a pentahedron, the tilter 211 may be embodied as a type of a triangular prism. Also, when the tilter 211 is a triangular prism type, a bottom angle of the triangular prism may range from 2 degrees to 45 degrees, for example. In addition to the range of 2 degrees to 45 degrees, the bottom angle of the triangular prism may variously range depending on the differing embodiments in the art.

The tilter 211 may be made of a material having a similar or an identical refraction index to the biological tissue of the body fat measurement object. Specifically, the tilter 211 may be made of a water epoxy in a solid type or a polymer based compound, for example.

As described herein, the light which is radiated from the light source 210 and penetrates into the biological tissue using the tilter 211, may more deeply penetrate into the biological tissue compared with light radiated from an optical sensor module lacking a tilter, such as shown in FIG. 2B.

As described in FIG. 2B, when a tilter 211 is not combined with the light source unit 230 of the optical sensor module, the light source unit 230 radiates light perpendicularly into a biological tissue. As described above, when the tissue is perpendicularly irradiated by the light, an optical path 231, i.e. the light reflected, absorbed, and scattered within the biological tissue, has a measurement depth as illustrated in FIG. 2B. Here, the light source unit 230 is inadequate because the light it radiates does not penetrate deeply enough into the biological tissue to accurately measure the thickness of the body fat.

However, as illustrated in FIG. 2A, when the tilter 211 is combined with the light source 210, the light may more deeply penetrate into the biological tissue. Specifically, as illustrated in FIG. 2A, the light radiated from the light source 210 may penetrate into the biological tissue, and may have a predetermined incidence angle upon the tissue, due to the tilter 211. In this instance, as illustrated in FIG. 2A, the optical path 212 penetrates deeper into the biological tissue, allowing measurement of the body fat thickness down to a muscle of the biological tissue.

Namely, when the light radiated from the light source 210 is irradiated into the biological tissue while having a predetermined tilt of the light using the tilter 211, the light may penetrate comparatively deeper into the biological tissue than when the biological tissue is perpendicularly irradiated by the light.

In some instances, increasing the distance between the optical detectors 220 and 240, and their respective light source units 210 and 230 may also increase the measurement depth allowing for the measurement of thicker layers of body fat. In an embodiment, the distance between the optical detectors 220 and 240, and their respective light source units 210 and 230, as shown in FIGS. 2A and 2B, is identical. In a further embodiment, regardless of whether the tilter 211 is provided as illustrated in FIG. 2A, the distance between the light source units 210 and 230, and the optical detectors 220 and 240 may be 20 mm. According to one or more embodiments, the light may penetrate deeper into the biological tissue by providing the tilter 211 to the light source 210, without extending the distance between the light source 210 and the optical detector 220. Accordingly, body fat may be consistently and accurately measured by using the optical path 212 having the deeper measurement depth, even when the thickness of the body fat is increased, which will be illustrated in FIG. 3.

Figure 3:
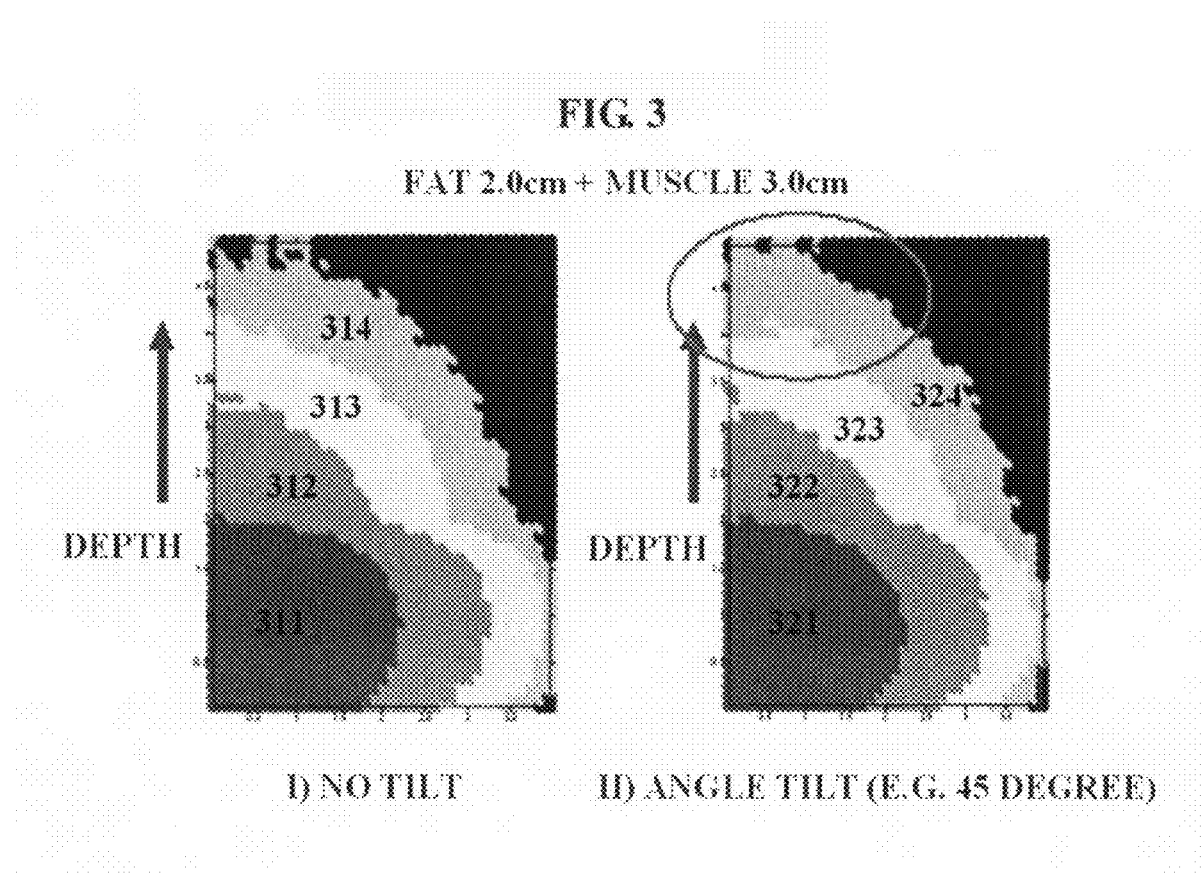
FIG. 3 illustrates simulation results of a body fat information measurement when a tilter is used with the light source unit, according to one or more embodiments of the present invention, in contrast with results when the tilter is not used with the light source unit.

FIG. 3, portions I and II, illustrate simulation results of a body fat measurement made: a) when a titter 211 is provided to the light source unit (portion II) according to one or more embodiments of the present invention; and b) when no tilter 211 is provided to the light source unit (portion I).

FIG. 3, portion I, illustrates the simulation results of the body fat measurement when a light, radiated from the light source, is irradiated into a biological tissue perpendicularly without providing the tilter 211 to the light source. Alternatively, FIG. 3, portion II, illustrates the simulation result of the body fat measurement when the light, radiated from the light source, is irradiated into the biological tissue, while having a tilt of 45 degrees, for example, by providing the tilter 211 to the light source, according one or more embodiments of the present invention.

The illustrated graphs of the body fat measurement show the simulation results for biological tissue having identical characteristics, i.e. the thickness of the body fat is 20 mm and the thickness of the muscle is 30 mm. A fat substitute having a thickness of 20 mm was also used for the simulation.

Here, the vertical axis in each graph of FIG. 3, portions I and II indicates a measurement depth, while the horizontal axis in each graph indicates a distance between a light source and an optical detector. Each area of the graphs of FIG. 3, portions I and II, i.e. a first area 311 and 321, a second area 312 and 322, a third area 313 and 323, and a fourth area 314 and 324, is shown in a different shade, in order to readily distinguish an irradiated optical power according to the distance between the light source and the optical detector.

Specifically, the first area 311 of portion I of FIG. 3 and the first area 321 of portion II of FIG. 3 indicate optical path information when the distance between the light source and the optical detector is identical, and identical optical power is used. Area 311 indicates optical path information when no tilter 211 is used while area 321 indicates optical path information when a tilter 211 is used according to one or more embodiments of the present invention.

The second area 312 of portion I of FIG. 3 and the second area 322 of portion II of FIG. 3 indicate optical path information when the distance between the light source and the optical detector is an identical second distance, and identical optical power is used. Area 312 indicates optical path information when no tilter 211 is used while area 322 indicates optical path information when a tilter 211 is used according to one or more embodiments of the present invention. The third area 313 of portion I of FIG. 3 and the third area 323 of portion II of FIG. 3 indicate optical path information when a distance between the light source and the optical detector is an identical third distance, and identical optical power is used. Area 313 indicates optical path information when no tilter 211 is used while area 323 indicates optical path information when a tilter 211 is used according to one or more embodiments of the present invention. Finally, the fourth area 314 of portion I of FIG. 3 and the fourth area 324 of portion II of FIG. 3 indicate optical path information when a distance between the light source and the optical detector is an identical fourth distance, and identical optical power is used. Area 314 indicates optical path information when no tilter 211 is used while area 324 indicates optical path information when a tilter 211 is used according to one or more embodiments of the present invention.

The above simulation demonstrates, as shown in the each graph of portions I and II of FIG. 3, that a deeper optical path is measured for each area of portion II of FIG. 3, compared to the corresponding area of portion I of FIG. 3. Specifically, when the fourth areas are compared in each graph, it can be seen that a deeper optical path is measured for the fourth area 324 of portion II of FIG. 3 than for the fourth area 314 of portion I of FIG. 3.

Accordingly, body fat may be accurately measured by providing a tilter 211 made of a material having a refraction index similar, or identical to, the body fat, without significantly extending a distance between the light source and the optical detector.

Also, according to another one or more embodiments of the present invention, the light source unit 112 may include at least two light sources. Here, the tilter 211 may be provided to any one of the light sources, which are included in the light source unit 112, which will now be described in greater detail by referring to FIG. 4.

Figure 4:
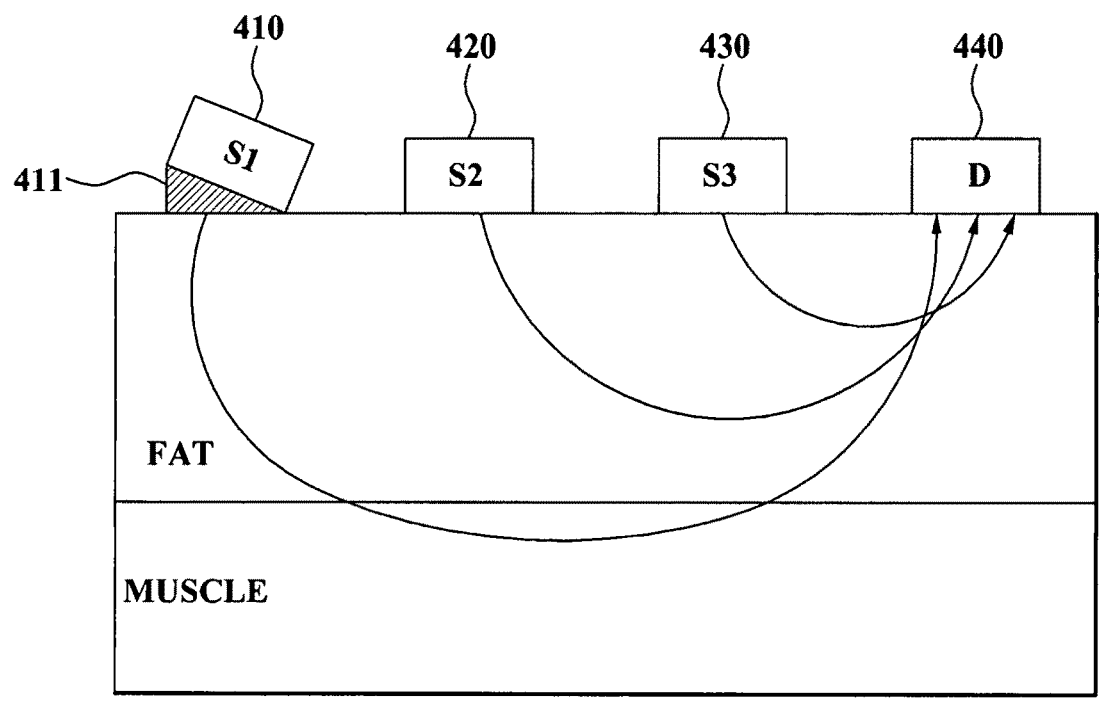
FIG. 4 illustrates an optical sensor module, according to one or more other embodiments of the present invention.

FIG. 4 illustrates an optical sensor module according to another one or more embodiments of the present invention.

Here, the optical sensor module may include a plurality of light sources. For convenience of description, an example in which the optical sensor module includes three light sources, i.e. a first light source 410, a second light source 420, and a third light source 430, is illustrated in FIG. 4, noting that alternative embodiments are equally available.

The first light source 410, the second light source 420 and the third light source 430 may be arranged with an optical detector 440, in parallel. In this non-limiting example, the tilter 411 may be provided to the first light source 410, however, depending upon embodiments, the tilter 411 may be provided with the first light source 410 and the second light source 420. Alternatively, the tilter 411 may be provided with the first light source 410, the second light source 420, and the third light source 430.

In yet another exemplary embodiment, the tilter 411 may be provided only to the first light source 410, as illustrated in FIG. 4. Specifically, the tilter 411 may be provided only to the first light source, that is, the light source farthest from the optical detector 440. This configuration may enable the radiated light to penetrate deeper into the biological tissue because the scattering path (i.e. the path of the irradiated light from the first light source 410 to the optical detector 440) is the longest.

Accordingly, when the tilter 411 is properly provided to the light source, body fat may be more accurately measured with reduced costs.

Referring back to FIG. 1, the optical power control unit 111 controls a driving current supplied to at least one light source, which may be included in the light source unit 112. Specifically, as described with reference to FIG. 4, when the light source unit 112 includes a plurality of light sources, the optical power control unit 111 may control the driving current, so that optical powers output from each of the light sources becomes greater, in proportion to the respective distances between each of the light sources and the optical detector 113.

The optical detector 113 receives light that has been scattered by biological tissue, the tissue having been irradiated by the light, and transforms the received scattered light into an electrical signal. Specifically, the optical detector 113 receives the scattered light from the biological tissue, i.e., at a measurement point, and transforms the scattered light into the electrical signal. For the above-described operation, the optical detector 113 may include a predetermined optical-electrical transducing element for transforming the optical signal into the electrical signal.

The electrical signal calculation unit 120 calculates body fat information at the measurement point by receiving the electrical signal. For the above operation, the electrical signal calculation unit 120 may include a signal amplification unit 121, a body fat information calculation unit 122, and an output control unit 123.

The signal amplification unit 121 transmits the transformed electrical signal into the body fat information calculation unit 122 after receiving and amplifying the transformed electrical signal.

The body fat information calculation unit 122 calculates body fat information at the measurement point using the amplified electrical signal. Specifically, the body fat information calculation unit 122 may calculate thickness of the body fat using the optical power of the scattered light from the biological tissue. The calculation may be based on the principal that scattering of light is greater in body fat and absorption of light is greater in muscle. Also, the body fat information calculation unit 122 may calculate the weight of the body fat, and may calculate a body fat ratio using a reference lookup table. Accordingly, the body fat calculation unit 122 may calculate the thickness of the body fat, the body fat ratio, the weight of the body fat, or other measures as would be appreciated by one skilled in the art.

In one embodiment, the output control unit 123 controls the body fat information to be displayed or played via the output unit 130. The output unit 130 may display or play the body fat information via the display unit 131 or via the sound output unit 132, respectively.

Accordingly, advantages of one or more embodiments of the present invention include acquiring body fat information about a deep body fat layer using a light source having a tilter. The tilter is formed of a material having a refraction index similar to the biological tissue being measured. The tilter may enable a light source to radiate light at a predetermined incident angle to penetrate deep into the biological tissue. The tilter may be generated along with the light sensor, e.g., they may be manufactured as a single unit, or they may operate independently as a system.

Further advantages of one or more embodiments of the present invention include an optical sensor module of a portable body fat measurement apparatus that may minimize a distance between a light source and an optical detector.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An optical sensor module for a body fat measurement apparatus, said apparatus being arranged to measure a thickness of a subcutaneous fat layer between skin and muscle in a biological tissue of an organism, the module comprising:
   at least one light source configured for use in a reflection scattering-absorption process;
   a tilter to control an irradiation angle of the at least one light source to radiate light from the at least one light source into the biological tissue at a predetermined angle other than an angle perpendicular to the biological tissue so that the radiated light penetrates deeper into the biological tissue, the tilter being placed between the at least one light source and the biological tissue whereby the light incident upon the biological tissue from the at least one light source falls substantially at an angle other than one perpendicular to the biological tissue;
   an optical detector to detect a scattered optical signal and to transform the scattered optical signal into an electric signal, the scattered optical signal being scattered from the light radiated into the biological tissue; and
   an optical power control unit to control a driving current applied to the at least one light source,
   wherein the optical detector further comprises a transformer unit to transform the scattered optical signal into an electrical signal, and
   wherein the irradiation angle is controlled such that the radiated light comprises
   a component directed away from the optical detector.

2. The module of claim 1, wherein the tilter is comprised of a material having a predetermined refraction index to radiate light from the at least one light source into the biological tissue at the predetermined angle.

3. The module of claim 1, wherein the tilter comprises a solid water epoxy or a polymer compound.

4. The module of claim 1, wherein the tilter is a prism and the irradiation angle ranges from 2 degrees to 45 degrees.

5. The module of claim 1, wherein:
   the at least one light source comprises at least two light sources, each being a different distance from the optical detector; and
   the tilter is located at one of the at least two light sources located farthest from the optical detector.

6. The module of claim 1, wherein:
   the electric signal is applied to an electric signal calculation unit; and
   the electric signal calculation unit receives the electric signal and calculates the thickness of the fat layer of a corresponding measurement point.

7. The module of claim 6, wherein the electric signal calculation unit comprises:
   a signal amplification unit to amplify the electric signal transformed by the transformer unit;
   a body fat information calculation unit to calculate body fat information comprising the thickness of the fat layer from the amplified electric signal; and
   an output control unit to control the body fat information to be output to a predetermined display unit or sound output unit.

8. A body fat measurement apparatus, said apparatus being arranged to measure a thickness of a subcutaneous fat layer between skin and muscle in a biological tissue of an organism, the apparatus comprising:
   at least one light source configured for use in a reflection scattering-absorption process;
   a tilter to control an irradiation angle of the at least one light source to radiate light from the at least one light source into the biological tissue at a predetermined angle other than an angle perpendicular to the biological tissue so that the radiated light penetrates deeper into the biological tissue, the titter being placed between the at least one light source and the biological tissue whereby the light incident upon the biological tissue from the at least one light source falls substantially at an angle other than one perpendicular to the biological tissue;
   an optical detector to detect a scattered optical signal and to transform the scattered optical signal into an electric signal, the scattered optical signal being scattered from the light radiated into the biological tissue;
   an electric signal calculation unit to process the electric signal and to calculate body fat information; and
   an optical power control unit to control a driving current applied to the at least one light source,
   wherein the irradiation angle is controlled such that the radiated light comprises
   a component directed away from the optical detector.

9. The apparatus of claim 8, wherein the tilter is comprised of a material having a predetermined refraction index to radiate the light from the at least one light source into the biological tissue at the predetermined angle.

10. The apparatus of claim 8, wherein the titter comprises a solid water epoxy or a polymer compound.

11. The apparatus of claim 8, wherein the tilter is a prism and the angle ranges from 2 degrees to 45 degrees.

12. The apparatus of claim 8, wherein:
   the at least one light source comprises at least two light sources respectively spaced apart, with the at least two light sources being a different distance from the optical detector; and
   the titter is located at one of the at least two light sources located farthest from the optical detector.

13. The apparatus of claim 8, wherein the electric signal calculation unit comprises:

a signal amplification unit to amplify the electric signal transformed by the optical detector;

a body fat information calculation unit to calculate the thickness of the body fat information comprising the thickness of fat layer from the amplified electric signal; and an output control unit to control the body fat information to be output to a predetermined display unit or sound output unit.

14. The apparatus of claim 8, wherein the body fat measurement apparatus is any one of a mobile communication terminal, a personal digital assistant (PDA), a portable game apparatus, an MP3 player, a personal multimedia player (PMP), a digital multimedia broadcasting (DMB) terminal, a portable blood sugar measurement apparatus, and a grip exercise apparatus.

15. A method for measuring body fat using an apparatus arranged to measure a thickness of a subcutaneous fat layer between skin and muscle in a biological tissue of an organism, the method comprising:

irradiating light, by way of at least one light source, into a biological tissue for use in a reflection scattering-absorption process, the light being radiated at a predetermined angle other than an angle perpendicular to the biological tissue so that the radiated light penetrates deeper into the biological tissue;

detecting, by way of an optical detector, light scattered from the irradiating of the light into the biological tissue; and transforming the detected scattered light into an electrical signal; and controlling a driving current applied to the at least one light source, wherein the irradiation angle is controlled such that the radiated light comprises a component directed away from the optical detector.

16. The method of claim 15 further comprising controlling a driving current applied to the at least one light source so that optical powers output from each of the at least one light source becomes greater in proportion to respective distances between each of the at least one light source and an optical detector.

17. The method of claim 15, further comprising calculating body fat information from the electrical signal.

18. The method of claim 15, further comprising:

amplifying the electrical signal;

calculating body fat information from the amplified electrical signal; and controlling the body fat information to be output to a predetermined display unit or sound output unit.

* * * * *